United States Patent [19]

De Boer

[11] Patent Number: 4,673,572
[45] Date of Patent: Jun. 16, 1987

[54] LIVE PURIFIED MAREK'S DISEASE VACCINE

[75] Inventor: Gerben F. De Boer, Lelystad, Netherlands

[73] Assignee: Centraal Diergeneeskundig Instituut, Netherlands

[21] Appl. No.: 720,176

[22] Filed: Apr. 5, 1985

[30] Foreign Application Priority Data

Apr. 9, 1984 [NL] Netherlands ................. 8401120

[51] Int. Cl.$^4$ .................... A61K 39/12; C12N 7/08
[52] U.S. Cl. .............................. 424/89; 435/237
[58] Field of Search ................. 424/89; 435/235, 237

[56] References Cited

U.S. PATENT DOCUMENTS

| | | | |
|---|---|---|---|
| 3,642,574 | 2/1972 | Okazaki et al. | 435/173 |
| 3,674,861 | 7/1972 | Churchill | 424/89 |
| 3,783,098 | 1/1974 | Calnek et al. | 435/239 |
| 4,160,024 | 7/1979 | Schat et al. | 424/89 |

OTHER PUBLICATIONS

Biostandards (IABS) Geneva, 29–42 (1972).
De Boer et al., J. Biol. Standard., 9: 15–22 (1981).
Bulow, Avian Pathology, 6: 395–403 (1977).
Calnek, J. Nat. Cancer Inst., 51: 929–939 (1973).
Churchill, et al., J. Gen. Virol., 4: 557–564 (1969).
Ikuta et al., J. Gen. Virol., 64: 2597–2610 (1983).
Maas et al., World's Poultry Sci. J., 38: 163–173 (1982).
Okazaki et al., Avian Diseases, 14: 413–429 (1970).
Payne et al., J. Nat'l. Cancer Inst., 39: 281–302 (1967).
Rispens et al., Avian Diseases, 16: 108–138 (1972).
Javma 183(3): 355, Abstract #139, and #140, Aug. 1, 1983.
Von Bulow et al., Avian Path., 4: 133–146 (1975).
Schat et al., J. Nat'l. Cancer Inst., 60: 1075–1082 (1978).
Witter, Avian Diseases, 27: 113–132 (1983).
Witter et al., Avian Path., 13: 75–92 (1984).

*Primary Examiner*—Esther M. Kepplinger
*Assistant Examiner*—Shawn P. Foley
*Attorney, Agent, or Firm*—Iver P. Cooper

[57] ABSTRACT

The invention relates to a highly immunogenic virus preparation derived by attenuation employing serial passages in avian cell cultures and six plaque purification steps from a Marek's disease virus strain, belonging to Avian Herpesvirus serotype-1. The original virus strain MDV CVI-988 was recovered from a healthy chicken (Avian Diseases 16: 108–125, 1972).

The live purified Marek's disease vaccine so obtained is innocuous for specific pathogen free Rhode Island Red chickens which are highly susceptible for development of Marek's disease tumors. The monovalent virus preparation, according to the invention, demonstrated in comparison with Marek's disease vaccines based on the same strain, currently in use at a lower cell passage level, an improved protective efficacy against challenge infection by two representatives of virulent Marek's disease virus.

The monovalent virus preparation, according to the invention, provided significantly better protection than current MDV CVI-988 vaccine to challenge infection with a representative of the group of newly emerging very virulent strains of Marek's disease virus, MDV RB/1B. The monovalent virus preparation, according to the invention, provided significantly better protection than is HVT FC126 vaccine to challenge infection with another representative of the group of very virulent MD viruses, MDV Tun.

5 Claims, No Drawings

LIVE PURIFIED MAREK'S DISEASE VACCINE

CROSS-REFERENCE TO RELATED APPLICATION

This application claims the benefit of the filing date of the Convention priority application Netherlands No. 8401120, filed Apr. 9, 1984, incorporated by reference herein.

BACKGROUND OF THE INVENTION

Marek's disease is a malignant lymphoproliferative disease of chickens, caused by an infection with Marek's disease virus, belonging to Avian Herpesvirus serotype-1 (Avian Pathology 4: 133-146, 1975). First recognized in 1907, it is still the most destructive of the poultry viruses.

The invention relates to a highly immunogenic and non-pathogenic virus preparation derived from Marek's disease virus (MDV) strain CVI-988, belonging to Avian Herpesvirus serotype-1, by serial passage in avian cell cultures and plaque purification. The original virus isolate, the parent strain MDV CVI-988, was recovered from a healthy laboratory chicken as an isolate of low virulence which could be attenuated by serial passages in cell cultures (Rispens et al. in Avian Diseases 16, pages 108-125 and 126-138 (1972)). Since then, the virus preparation obtained after about 35 passages in avian cell cultures has been used succesfully for vaccination of chickens against Marek's disease (MD). Initially, the virus attenuation had been carried out in duck embryo fibroblasts (DEF). However, ducks are difficult to maintain under specific pathogen free (SPF) conditions. This necessitates extensive testing of every production batch in order to guarantee the absence of micro-organisms pathogenic to birds. Maintenance of chickens under SPF conditions creates less problems. Moreover, chicken cells are preferred because they will not introduce, into the MD vaccines, cells foreign to the animal species. Consequently, in the period of 1967-1978 the MDV CVI-988 strain was adapted to chick embryo fibroblast cell cultures (CEF) and the MDV CVI-988 vaccine producers switched to vaccine production in CEF.

Although, in practice, vaccines based on the parent strain MDV CVI-988 provide highly satisfactory results via intramuscular administration (Maas et al., World Poultry Sci. 38, 163-176 (1982)), subcutaneous application is less effective, it may provoke MD lesions in chickens of the strain of highly MD susceptible SPF Rhode Island Red (RIR) chickens, when these chickens are inoculated with ten times the normal field dose (Avian Pathology, 6, 395-403 (1977)).

In JAVMA vol. 183, page 355, K. A. Schat, et al. reported that a new clone of the JM strain of Marek's disease (JM-16) and certain of its subclones did not induce tumors, but immunogenicity was not discussed.

On the same page G. F. De Boer et al. discussed an MDV CVI-988 clone obtained by passage in cell cultures and plaque purification of MDV CVI-988. Passages no. 51 and no. 97 were safe in RIR chickens, and effective protection was obtained in a small number of vaccination trials with passage no. 51, but not with passage no. 97. Passage no. 51 gave about the same degree of protection as the commercial parent vaccine (passage no. 35). The abstract did not disclose any deposit numbers under which cultures of these new clones might be requested. Moreover, the clones discussed have been found to be inferior to CVI-988 CEF$_{65}$ clone C in immunogenicity.

Other vaccines against Marek's disease in use are:

A. A vaccine based on a Turkey Herpesvirus (HVT FC126), ((Avian Diseases 14, pages 413-429 (1970)) and U.S. Pat. No. 3,642,574)) belonging to Avian Herpesvirus serotype-3. Application in cell-free form of this vaccine is described in U.S. Pat. No. 3,783,098.

B. A vaccine obtained by attenuation of a virulent MDV strain (HPRS-16), ((Journal of General Virology 4, 557-564 (1969) and U.S. Pat. No. 3,674,861)) belonging to Avian Herpesvirus serotype-1.

C. A vaccine based on a non-oncogenic virus strain of Marek's disease virus of serotype-2 (SB-1), ((Journal National Cancer Institute 60, 1075-1082 (1978), and U.S. Pat. No. 4,160,024)). This vaccine to be effective is generally applied as a mixture with HVT vaccine.

SUMMARY OF THE INVENTION

According to the present invention a virus preparation, especially a vaccine, is provided which is highly immunogenic and non-pathogenic in poultry, and particularly in chickens.

The virus preparation according to the invention comprises a clone of MDV belonging to Avian Herpes virus serotype-1 which has been obtained from the virus isolate MDV CVI-988 by serial passages in DEF and six plaque purification steps between DEF passages No. 39 and No. 49. This virus clone, which is called MDV CVI-988 clone C, has been selected because of being highly immunogenic and being not pathogenic to RIR chickens.

In view of its use as seed virus in vaccine production the virus clone in question was adapted to CEF by means of alternating virus passages in CEF and DEF between cell culture passage Nos. 52 and 63. This clone, in the 65th CEF passage (MDV CVI-988 CEF$_{65}$ clone C) has been deposited on Mar. 28th 1984, under number PC PV 1 in the Phabagen Collection, Vakgroep Moleculaire Biologie, Transitorium 3, Padualaan 8, 3584 CH Utrecht, the Netherlands.

In addition, a deposit has been made on 19.03.1985 at the Collection Nationale de Cultures de Micro-organismes, Institut Pasteur, 28, Rue du Docteur Roux, 75015 Paris, France, under number C.N.C.M.I-426. CVI-988 CE$_{65}$ clone C is also deposited with the American Type Culture Collection as strain VR2103, received by ATCC on July 2, 1985.

One object is to provide a Marek's disease virus preparation which is nonpathogenic to poultry in general, and chickens in particular, even to Rhode Island Red chickens which are highly MD susceptible.

Another object of the invention is to provide a Marek's disease virus preparation which is highly immunogenic.

Another object of the invention is to provide a Marek's disease virus preparation which is capable of protecting inoculated chickens against virulent and very virulent strains on Marek's disease virus.

Another object of the invention is to provide a clone of the Marek's disease virus which is derived from the parent strain MDV CVI-988 but which is substantially less pathogenic without loss of immunogenicity.

Another object of the invention is to provide a family of clones of the Marek's disease virus, Avian Herpesvirus serotype-1, by serial passages in avian cell cultures and plaque purification, whereby a strain may be selected with a favorable combination of nonpathogenicity and immunogenicity.

Another object of the invention is to provide a vaccine capable of protecting against very virulent MD viruses which does not include serotype-2 or serotype-3 components.

Other objects of the invention will be evident after consideration of these specifications and claims.

DETAILED DESCRIPTION OF THE PREFERRED EMBODIMENTS

Three serotypes of Avian Herpersvirus are recognized. Pathogenic MDV strains belong to Avian Herpesvirus serotype-1, nononcogenic MDV strains are serotype-2 and Turkey Herpesvirus (HVT) strains are serotype-3 (Avian Pathology, 4: 133–146, 1975).

Vaccines made from HVT strains protect chickens aganst virulent strains which all belong to serotype-1. However, "very virulent" strains emerged against which serotype-3 vaccines afforded inadequate protection (Avian Diseases 27: 113–132, 1983). These "very virulent" strains can be controlled by bivalent vaccines comprising both serotype-2 (MDV SB-1) and serotype-3 (HVT). Use of a trivalent vaccine including an attenuated serotype-1 MD virus, MD 11/75C, has also been described (Avian Pathology, 13: 75–92, 1984).

The invention relates to a highly immunogenic virus preparation containing a live virus clone of Marek's disease virus belonging to Avian Herpes virus serotype-1 obtained by serial passages in avian cell cultures and plaque purification of the virus MDV CVI-988, which clone is capable of protecting chickenss inoculated with said clone against subsequent challenge infection by virulent and very virulent MD viruses, such as MDV K, MDV GA-5, MDV RB/1B and MDV Tun, and is substantially nonpathogenic to highly MD susceptible SPF RIR chickens.

Production of Experimental Vaccine

The virus strain was attenuated by means of 51 serial passages in DEF, including six plaque purification steps between DEF passages No. 39 and No. 49, in which the virus harvest of one localized cytopathological change (virus plaque or focus) was used as the inoculum. Clone C was selected at the final plaque purification step. Such monolayers were inoculated with end-point dilutions of the virus, and the newly-formed virus was localized in situ by the addition of 0.85% agar to the medium. Adaptation to CEF was obtained by alternating passages in CEF and DEF between passages Nos. 52 and 63, and thereafter cell culture passages were carried out in CEF. After a culture period of 3 to 5 days, depending on the virus dose in the inoculum, specific cytopathological changes are detectable.

Duck embryo fibroblasts were obtained by trypsinization of embryos from 13 day-old embryonated duck eggs. Culture vessels (Petri dishes or Roux bottles) were seeded with cell suspensions containing $0.8\times10^6$ cells per ml. The cultures were incubated at 38.5° C. in a medium in which the $CO_2$ percentage was maintained at 5%. The growth medium had the following composition:

| | |
|---|---|
| Demineralized water | 818 ml |
| Medium 199 (10x concentrated) | 90 ml |
| $NaHCO_3$, 1.4% | 87 ml |
| Calf serum | 60 ml |
| Sodium benzyl penicillin (50,000 I.U./ml) | 5 ml |
| Streptomycin sulphate (50,000 I.U./ml) | |
| Pimafucin ® (0.25%/ml) | |
| Vitamin concentrate (BME, Gibco) | 1 ml |
| Glutamine 2.6% | 3,8 ml |

After a culture period of 2 days coherent monolayers are formed, and the infection is carried out by inoculation with a suspension of infected cells from the previous virus passage. According to the degree of cytopathic effect the cells from each infected culture were used to infect 4 to 20 fresh cultures. From this moment on the maintenance medium contains:

Demineralized water: 810 ml
Medium F-10(10x): 50 ml
Medium 199(10x): 40 ml
Tryptose phosphate broth: 40 ml
$NaHCO_3$, 1.4%: 75 ml
Calf serum: 30 ml
Antibiotics etc. as mentioned above.

Eleven day-old embryonated eggs from an SPF poultry flock were used for the preparation of CEF monolayers. The culture media were as mentioned above. In the period wherein the virus strain was not maintained by means of virus multiplication in DEF or CEF, the virus was stored in liquid nitrogen at −196° C. The freezing of the infected cells was done in growth medium, mentioned above, with calf serum increased to 10% and the same percentage dimethyl sulphoxide (DMSO). The cooling rate in the range +20° C. to −40° C. was automatically controlled at a rate of 1° C. per minute. An estimate of the virus titre of the vials was made by a plaque assay in CEF.

Intramuscular inoculation of the chickens was carried out immediately after reconstitution of the vaccine. The maintenance medium described above was a suitable diluent. Each bird received an inoculum of 0.5 ml containing the desired dosage of cell-associated MD virus.

Large Scale Production

Commercial Marek's disease vaccines are produced in principle, in a similar way as in the research laboratory. In view of the larger scale rolling bottle systems instead of stationary culture vessels (Roux bottles) are used. Checks of the seed material, progress checks during production, tests with the end product with respect to the absence of extraneous micro-organisms and with respect to virus content are carried out according to the directives as established by an international group of experts (Report of the Avian Products Standardization Committee of the International Association of Biological Standardization, E. C. Hulse et al. eds. pages 29–42, Geneva, Switzerland: Biostandards). With respect to activity Marek's disease vaccines should meet the requirement of a certain protective index. This can be described as the ratio between the percentages of diseased test animals in vaccinated and non-vaccinated groups following challenge infection and within a predetermined period of time. A more accurate method for the estimation of the immunogenic properties of the virus preparation involves a fifty percent protective dose assay ($PD_{50}$) as described in Journal of Biological Standardization 9, 15–22 (1981).

CHARACTERISTICS OF THE LIVE PURIFIED MD VACCINE

Innocuity for RIR chickens

As indicated in the introduction the current available MD vaccines based on strain MDV CVI-988, used in the 35th tissue culture passage, offer satisfactory protection in the field. The vaccine, however, induces MD lesions in SPF RIR chickens which are highly MD susceptible. The pathogenic properties of a number of MDV CVI-988 clones were studied in SPF RIR chickens.

These studies were initiated because earlier it was shown that MDV CVI-988 $DEF_{51}$ clone C and MDV CVI-988 $DEF_{97}$ clone E were not pathogenic to SPF RIR chickens. The innocuity studies performed with MDV CVI-988 $DEF_{51}$ clone C, MDV CVI-988 $CEF_{59}$ clone C and MDV CVI-988 $CEF_{65}$ clone C are illustrated in examples I and II. They show that the virus clone C according the invention is non-pathogenic to RIR chickens. The innocuity studies performed with MDV CVI-988 $CEF_{63}$ clone A, MDV CVI-988 $CEF_{62}$ clone B, MCV CVI-988 $CEF_{67}$ clone C' and MDV CVI-988 $CEF_{59}$ clone C', the latter two originating from plaque C, collected from DEF passage no. 49, but with slightly different cell passage history, are illustrated in example III. These experiments demonstrate that in two chickens, one inoculated with clone A and the other with clone C', histological lesions specific for Marek's disease were observed.

Protective efficacy

Virus clone C of the present invention is highly efficacious in protecting poultry against MD when challenged by a variety of known virulent MD strains such as MDV K and MDV GA-5, and two very virulent strains, MDV RB/1B and MDV Tun.

The gradual reduction of 'A' antigen

The 'A' antigen was originally detected both in cell extracts and culture fluids of MD virus infected cells by immunodiffusion analysis (J. Gen. Virol. 4, 557–564, 1969). The 'A' antigen is thought to be composed of glycoproteins ranging from molecular weight 54K to 70K (J. Gen. Virol. 64, 2597–2610, 1983).

The cell culture passage history of the various MDV CVI-988 batches examined for the presence of 'A' antigen is acronymically designated as follows:

MDV CVI-988 $CEF_{37}$ ($DEF_{1-4}$, $CEF/DEF_{5-14}$, $CEF_{15-37}$)

MDV CVI-988 $CEF_{65}$ clone C ($DEF_{1-51}$, $CEF/DEF_{52-57}$, $CEF_{58-59}$, $DEF/CEF_{60-65}$, plaque purification steps between passage nos. 39 and 49)

MDV CVI-988 $DEF_{99}$ clone E ($DEF_{1-99}$, plaque purification steps between passage nos. 87 and 94).

MDV CVI-988 $DEF_{166}$ ($DEF_{1-166}$).

Supernatant fluids of MDV CVI-988 $CEF_{37}$, MDV CVI-988 $CEF_{65}$ clone C, MDV CVI-988 $DEF_{99}$ clone E and MDV CVI-988 $DEF_{166}$ were tested for the presence of 'A' antigen by immunoprecipitation studies employing a rabbit serum directed to MDV-gp 54/70 (kindly provided by Dr. L. Velicer, Lansing, MI, USA).

'A' antigen was not detected in MDV CVI-988 $DEF_{166}$ supernatant fluid, but was produced in cell cultures infected with passage nos. 35, 65 and 99. During serial cell culture passages and plaque purifications a gradual reduction of the amount 'A' antigen produced, was observed. Roughly the amount of 'A' antigen produced by MDV CVI-988 $CEF_{65}$ clone C was about 90% below the 'A' antigen expression by MDV CVI-988 $CEF_{37}$.

Since the virus preparation of the invention (MDV CVI-988 $CEF_{65}$ clone C) may be considered as fully attenuated, with respect to pathogenicity to highly susceptible RIR chickens, the conclusion is warranted that MDV attenuation can not always be associated with complete loss of 'A' antigen expression.

INNOCUITY STUDIES

EXAMPLE I

Determination of the pathogenicity of MDV CVI-988 $DEF_{51}$ clone C with respect to RIR chickens in comparison with that of HVT FC126 and MCV CVI-988 $CEF_{35}$.

The test was carried out with spf RIR chickens of the Houghton Poultry Research Station (England). The chickens were kept in modified Horsfall-Bauer isolators. The birds were fed ad libitum with all mash meal feeds. They were examined daily, during 24 weeks, for the occurrence of clinical symptoms of MD. The chickens were, as one-day-old chickens, inoculated intramuscularly with 10,000 FFU of the virus in question in 0.5 ml tissue culture medium, which corresponds to ten times the usual field dosage. All the vaccine preparations contained the virus in cell-associated form.

A group of 20 RIR chickens was inoculated with MDV CVI-988 $CEF_{35}$ the commercial vaccine. Another group of 20 RIR chickens obtained the virus preparation according to the invention (MDV CVI-988 $DEF_{51}$ clone C). A group of 43 RIR chickens was inoculated with HVT FC126.

Dead and moribund birds were removed and subjected to autopsy. The tissues were examined microscopically. At the end of the observation period all of the remaining chickens were killed and examined macroscopically and microscopically. Nerve lesions were classified according to Payne and Biggs, Journal of the National Cancer Institute 39, 281–302 (1967) as inflammatory (B-type) lesions and lymphomatous (A-type) lesions. Increased lymphoid infiltration and lymphocytic hyperplasia in visceral organs were considered to be signs of Marek's disease. The total number of chickens was corrected for aspecific mortality within 21 days after hatching.

The results are shown in Table 1. It mentions the ratio of the number of chickens showing macroscopic pathological and/or microscopical signs of MD with respect to the total number of chickens subjected to the test. The inoculation of RIR chickens with the commercial vaccine (MDV CVI-988 $CEF_{35}$) induced paralysis in 5 of 8 chickens. The paralysis was accompanied by endoneural inflammation of peripheral nerves and nerve plexi (B-type lesions). Another two chickens were removed when moribund. These chickens also showed B-type lesions in peripheral nerves. One chicken which died during the test did not show any sign of Marek's disease. In the first two weeks 12 chickens died by accidental causes.

Neither macroscopical signs nor microscopical lesions were seen in the group of RIR chickens inoculated with the vaccine preparation according to the invention. Paralysis was however observed in one RIR chicken which had been inoculated with HVT FC126. Microscopical examination of the peripheral nerves revealed small lesions characteristic for an endoneural lymphoma. At the end of the observation period microscopical examination disclosed B-type lesions in peripheral nerves of 3 chickens inoculated with HVT FC126. One chicken with clinical paralysis showed a non-specific neuritis.

EXAMPLE III

Similar innocuity tests employing RIR chickens, as described in example I and II, were performed with the clones A, B and C' which all originated from MDV CVI-988 DEF passage no. 48. (Both clone C' and clone C originated from the same plaque in DEF passage no. 49). Clone D was tested in addition.

MDV CVI-988 CEF$_{63}$ clone A:

Sixteen RIR chickens, hatched from SPF RIR eggs obtained from Wickham Laboratories, were intramuscularly inoculated with 10.000 FFU immediately after hatching. The test procedure was similar to the procedure of example II.

Clinical or macroscopical signs of Marek's disease were not observed. However, at histological examination inflammatory lesions, B-type lesions according to Payne and Biggs, J. Natl. Cancer Institute 39, 281–302 (1967), were observed in the nerve plexus of one out of 10 chickens necropsied at 24 weeks.

MDV CVI-988 CEF$_{62}$ clone B:

Eighteen RIR chickens hatched from SPF RIR eggs obtained from Wickham Laboratories, were intramuscularly inoculated with 10.000 FFU of clone B. The test procedure was similar to the procedure of example II. Neither clinical nor macroscopical signs of Marek's disease nor histological lesions associated with MD were observed in any of the 18 test chickens.

MDV CVI-988 CEF$_{67}$ clone C':

Fourteen RIR chickens hatched from SPF RIR eggs obtained from Wickham Laboratories, were intramuscularly inoculated with 10.000 FFU of clone C', which underwent cell passages in DEF up to passage no. 54. The test procedure was similar to the procedure of example II. Neither clinical nor macroscopical signs of Marek's disease nor histological lesions associated with MD were observed in any of the 14 test chickens.

MDV CVI-988 CEF$_{59}$ clone C':

Thirteen RIR chickens hatched from SPF RIR eggs obtained from Wickham Laboratories, were intramuscularly inoculated with 10.000 FFU immediately after hatching.

After an observation period of 24 weeks the test was terminated by autopsy. Three chickens died of non-specific causes performed on the remaining 10 chickens (6 ♀ and 4 ♂).

Neither clinical nor macroscopical signs of Marek's disease were observed in any of the 10 chickens.

Histological examination was performed on thymus, bursa of Fabricius, liver, both vagal and intercostal nerves and brachial and sciatic nerves and nerve plexuses from both sides. In one chicken (♀) an inflammatory B-type lesion was observed in the sciatic nerve.

TABLE 1

Comparison of two commerical vaccines with the vaccine according to the invention pathogenic properties in RIR chickens

| Inoculum | Number of chickens | Aspecific mortality[1] | Mortality within 24 weeks | | | | Autopsy after 24 weeks | | Number of MD pos/ total number of chickens[2] |
|---|---|---|---|---|---|---|---|---|---|
| | | | nerve swelling | B type lesions | A type lesions | MD neg. | B type lesions | MD-neg | |
| MDV CVI-988 CEF$_{35}$ | 20 | 12 | 5 | 7 | — | 1 | — | — | 7/8(88%) |
| MDV CVI-988 DEF$_{51}$ clone C | 20 | 2 | — | — | — | — | — | 18 | 0/18(0%) |
| HVT FC126 | 43 | 4 | — | — | 1 | 2 | 3 | 33 | 4/39(10%) |
| Control | 20 | 3 | — | — | — | — | — | 17 | 0/17(0%) |

[1]Aspecific mortality within 21 days after hatching.
[2]Total number of chickens is corrected for aspecific mortality.

EXAMPLE II

Similar innocuity tests employing RIR chickens, as described in example I, were performed with two CEF adapted preparations of the invention (MDV CVI-988 CEF$_{65}$ clone C and MDV CVI-988 CEF$_{59}$ clone C).

MDV CVI-988 CEF$_{65}$ clone C:

Twenty RIR chickens, hatched from SPF RIR eggs obtained from Wickham Laboratories, were intramuscularly inoculated with 10,000 FFU immediately after hatching. The chickens were maintained in modified Horsefall-Bauer isolators.

Ten weeks after inoculation 6 chickens were removed from the isolator (5 males, 1 female) and necropsied. Histologic examination was performed on thymus, bursa of Fabricius, spleen, liver, both vagal and intercostal nerves, and trachial and sciatic nerves and nerve plexuses from both sides.

After an observation period of 24 weeks the test was terminated by autopsy performed on the remaining 10 female chickens. The tissues selected for histological examination were as described above.

Neither clinical nor macroscopical signs of Marek's disease nor histological lesions associated with MD were observed in any of the 16 test chickens.

MDV CVI-988 CEF$_{59}$ clone C:

Thirteen RIR chickens, hatched from SPF RIR eggs obtained from Wickham Laboratories, were intramuscularly inoculated with 10,000 FFU immediately after hatching. The chickens were maintained in modified Horsefall-Bauer isolators.

Two chickens died of non-specific causes. After an observation period of 24 weeks the test was terminated by autopsy performed on the remaining 11 chicken (5 ♀ and 6 ♂). Neither clinical nor macroscopical signs of Marek's disease were observed in any of the 11 chickens.

Histological examination was performed on thymus, bursa of Fabricius, spleen, liver, both vagal and intercostal nerves and brachial and sciatic nerves and nerve plexuses from both sides.

In one chicken (♂) a lymphoid hyperplasia was observed in the liver. Bursa-dependent follicular structures were observed, the lesions were therefore not considered to be neoplastic.

MDV CVI-988 DEF$_{97}$ clone D

Twenty RIR chickens hatched from SPF RIR eggs obtained from the Houghton Poultry Research Station (England), were intramuscularly inoculated with 10.000 FFU of clone D. Alike clone E, this clone D underwent cell culture passages in DEF only, and plaque purification steps were performed between passages Nos. 87 and 94. Two chickens died of aspecific causes. The test procedure was similar to the procedure of example I. Neither clinical nor macroscopical signs of Marek's disease or histological lesions associated with MD were observed in any of the 18 test chickens.

PROTECTIVE EFFICACY STUDIES

The immunogenic properties of a vaccine preparation is most accurately determined by a 50% protective dose (PD$_{50}$) assay (Journal of Biological Standardization 9: 15–22, 1981).

The PD$_{50}$ is defined as the number of plaque or focus forming units (FFU)—determined in an in vitro test—necessary to protect 50% of the MD-susceptible part of a group of SPF chickens against clinical symptoms and lesions of Marek's disease. The challenge is conducted on the 9th day of life by intramuscular injection with virulent MDV in a dosage which is known to provoke in unvaccinated chickens more than 70% MD lesions during an observation period of 10 weeks. The test results so obtained can be processed statistically by means of a computer program, developed by the UCLA Health Sciences Computing Facilities (BMD03S, version of June 1st, 1964). Further information about the use of this statistical method is given in Journal of Biological Standardization 9: 15–22, 1981. Said computer program allows probit analysis of the test results and determination of the slope of the probit regression lines. A PD$_{50}$ is calculated on the basis of pathological phenomena in that part of the test animals possessing MD-susceptibility. The natural resistance is expressed in the control groups.

The protective efficacy studies with various virus clones (not clone C) obtained from strain MDV CVI-988, employing intramuscular administration, yielded the following results:

MDV CVI-988 CEF$_{55}$ clone A:

The protective efficacy of clone A was very poor. The PD$_{50}$ trial yielded a flat dose response line, with virus doses of 100 and 500 FFU respectively 19 and 7 chickens of 40 test chickens were protected against MDV-K challenge.

MDV CVI-988 CEF$_{55}$ clone B:

The PD$_{50}$ trial performed with a CEF adapted preparation of clone B yielded a PD$_{50}$ estimate of 31.9 FFU, which was significantly higher than the PD$_{50}$ estimate obtained for MDV CVI-988 CEF$_{59}$ clone C ($p<0.05$).

MDV CVI-988 CEF$_{59}$ clone C':

The PD$_{50}$ trial performed with a CEF adapted preparation of clone C' yielded a PD$_{50}$ estimate of 41.6 FFU, which was significantly higher than the PD$_{50}$ estimate obtained for MDV CVI-988 CEF$_{59}$ clone C ($p<0.05$).

MDV CVI-988 DEF$_{97}$ clone D:

This clone D was shown to be overattenuated. A relatively small number of chickens was protected against MDV-K challenge.

Based on the innocuity and protective efficacy studies it was concluded that MDV CVI-988 clone C was the best candidate for development of a Marek's disease vaccine.

The protective efficacy of the virus clone according to the invention is illustrated in examples IV to VIII.

EXAMPLE IV

Determination of the immunogenicity of MDV CVI-988 DEF$_{51}$ clone C in comparison with that of MDV CVI-988 CEF$_{35}$ and HVT FC126.

In this test the immunogenic activity of a virus preparation according to the invention, MDV CVI-988 DEF$_{51}$ clone C was compared with two preparations widely used in practice, viz. MDV CVI-988 CEF$_{35}$ and HVT FC126. To this end the PD$_{50}$ was determined, which is defined as the number of FFU required to protect 50% of the MD-susceptible part of a group of chickens from clinical symptoms and/or macroscopical lesions of MD.

Challenge infection was done at 9 days of age with a virulent MDV clone GA-5 (Journal of the National Cancer Institute 51, 929–939(1973)).

SPF chickens, White Leghorn, strain A (WLA) were used. The various groups of test chickens were held in modified Horsefall-Bauer isolators. The chickens of each of the dosage groups were divided over two isolators. The birds were fed ad libitum with all mash meal feeds.

After inoculation the virus preparations were subjected to plaque titration in CEF or in DEF. The chickens were observed for clinical symptoms of MD. During this period dead or diseased birds were removed from the isolators. At the end of the test period all of the remaining birds were also examined for symptoms of MD.

Table 2 shows the number of chickens showing clinical symptoms and/or macroscopical lesions of MD and the total number of test animals per dosage group. Each of the tested virus preparations gave protection against intramuscular infection with MDV GA-5, the highest virus dosage being most effective. Probit analysis of the data obtained from the three tests allowed calculation of PD$_{50}$ values between 14 and 33 FFU. Significant differences were not observed between the PD$_{50}$ values of the three virus preparations tested.

TABLE 2

Comparison of three PD$_{50}$ assays performed with MDV CVI-988 DEF$_{51}$ clone C, MDV CVI-988 CEF$_{35}$ and HVT FC126.

|  | Vaccine | | |
| --- | --- | --- | --- |
|  | MDV CVI-988 DEF$_{51}$ clone C | MDV CVI-988 CEF$_{35}$ | HVT FC126 |
|  | Challenge virus | | |
|  | GA-5 | GA-5 | GA-5 |
| Highest dose (FFU) | 1000 | 500 | 500 |
| Serial dilutions in steps | 1:5 | 1:5 | 1:5 |
| Number protected/total |  |  |  |
| Highest dose | 28/30 | 24/27 | 30/31 |
|  | 29/32 | 21/24 | 30/32 |

TABLE 2-continued

Comparison of three PD$_{50}$ assays performed with MDV CVI-988 DEF$_{51}$ clone C, MDV CVI-988 CEF$_{35}$ and HVT FC126.

|  | Vaccine | | |
| --- | --- | --- | --- |
|  | MDV CVI-988 DEF$_{51}$ clone C | MDV CVI-988 CEF$_{35}$ | HVT FC126 |
|  | Challenge virus | | |
|  | GA-5 | GA-5 | GA-5 |
|  | 25/31 | 18/26 | 21/31 |
|  | 12/32 | 9/23 | 8/32 |
| Lowest dose | 9/32 | | |
| No vaccine | 3/32 | 5/22 | 4/28 |
| PD$_{50}$* | 33 | 14 | 14.7 |
| 95% Confidence interval of PD$_{50}$ | 16.5–66 | 4.4–44.9 | 6.7–32.1 |
| Slope of probit regression line | 1.07 | 0.87 | 1.50 |
| Standard error of slope | 0.18 | 0.23 | 0.27 |

*The number of FFU required to protect 50% of the MD susceptible chickens.

EXAMPLE V

The same tests as in example IV were carried out with the virus preparations MDV CVI-988 DEF$_{54}$ clone C' and -CEF$_{54}$ clone C, according to the invention, in comparison with MDV CVI-988 CEF$_{35}$ and the HVT FC126+MDV SB-1 mixture. The challenge infection was performed with virulent MDV-K.

The results are presented in Table 3.

lates from problem flocks in the USA. This particular isolate was recovered in the USA from an HVT vaccinated layer flock, and was kindly provided by Dr. K. A. Schat, Ithaca, N.Y..

The significance of the differences observed between pairs of PD$_{50}$ estimates, obtained in the various assays were determined by a computer program derived from the log-likelihood-ratio test (Kendall and Stuart, In: The Advanced Theory of Statistics, vol. 2, 3rd edition

TABLE 3

Comparison of four PD$_{50}$ assays, with MDV CVI-988 DEF$_{54}$ clone C', MDV CVI-988 CEF$_{54}$ clone C, MDV CVI-988 CEF$_{35}$ and the HVT FC126 + MDV SB-1 mixture.

|  | Vaccine | | | |
| --- | --- | --- | --- | --- |
|  | MDV CVI-988 DEF$_{54}$ clone C' | MDV CVI-988 CEF$_{54}$ clone C | MDV CVI-988 CEF$_{35}$ | HVT FC126 + MDV SB-1 |
|  | Challenge virus | | | |
|  | K | K | K | K |
| Highest dose (FFU) | 500 | 500 | 500 | 500 |
| Serial dilutions in steps | 1:5 | 1:5 | 1:5 | 1:5 |
| Number protected/total | | | | |
| Highest dose | 28/30 | 29/29 | 30/30 | 27/27 |
|  | 17/30 | 26/29 | 25/29 | 26/29 |
|  | 13/28 | 25/30 | 22/29 | 24/29 |
| Lowest dose | 12/30 | 18/28 | 14/30 | 22/29 |
| No vaccine | 10/28 | 15/29 | 7/30 | 12.29 |
| PD$_{50}$* | 26.5 | 12.9 | 10.3 | 6.4 |
| 95% Confidence interval of PD$_{50}$ | 10.8–64.8 | 3.4–48.5 | 3.3–32.1 | 0.48–85.4 |
| Slope of probit regression line | 1.24 | 1.22 | 1.20 | 0.79 |
| Standard error of slope | 0.34 | 0.42 | 0.29 | 0.30 |

*The number of FFU required to protect 50% of the MD susceptible chickens.

EXAMPLE VI

The same PD$_{50}$-determination as described in examples IV and V was carried out with three virus preparations according to the invention, MDV CVI-988 DEF$_{54}$ clone C', MDV CVI-988 CEF$_{54}$ clone C and MDV CVI-988 CEF$_{65}$ clone C, in comparison with the commercial preparation MDV CVI-988 CEF$_{35}$. The challenge infection was carried out with MDV RB/1B. This virus is a representative of very virulent MD iso- Charles Griffin & Co. Ltd. London 24: 234–272 1973)). The PD$_{50}$ assays were comparable if the same strain of experimental chickens were employed, if the MD symptoms and lesions were scored by macroscopical inspection only and if the challenge infection was either by a virulent MDV or by a very virulent MDV. This statistical evaluation is only feasible if the slopes of the compared probit regression lines and the natural resistance to MD development of both series are not significantly different.

TABLE 4

Comparison of four $PD_{50}$ assays performed with MDV CVI-988 $DEF_{54}$ clone C', MDV CVI-988 $CEF_{54}$ clone C, MDV CVI-988 $CEF_{65}$ clone C and MDV CVI-988 $CEF_{35}$.

|  | Vaccine | | | |
|---|---|---|---|---|
|  | MDV CVI-988 $DEF_{54}$ clone C' | MDV CVI-988 $CEF_{54}$ clone C | MDV CVI-988 $CEF_{65}$ clone C | MDV CVI-988 $CEF_{35}$ |
|  | Challenge virus | | | |
|  | RB/IB | RB/IB | RB/IB | RB/IB |
| Highest dose (FFU) | 2500 | 2500 | 560 | 2500 |
| Serial dilutions in steps | 1:5 | 1:5 | 1:5 | 1:5 |
| Number protected/total |  |  |  |  |
| Highest dose | 23/23 | 21/21 | 40/41 | 20/20 |
|  | 23/24 | 17/20 | 39/40 | 20/20 |
|  | 19/24 | 20/20 | 33/41 | 15/20 |
| Lowest dose | 9/24 | 16/19 | 17/38 | 9/20 |
| No vaccine | 0/25 | 0/18 | 4/38 | 2/20 |
| $PD_{50}$* | 31.6 | ** | 6.5*** | 34.3 |
| 95% Confidence interval of $PD_{50}$ | 6.9–144 |  | 2.0–21.5 | 5.6–211 |
| Slope of probit regression line | 1.53 |  | 1.19 | 1.73 |
| Standard error of slope | 0.34 |  | 0.22 | 0.48 |

*The number of FFU required to protect 50% of the MD susceptible chickens.
**Due to the irregular course of the dose response line the $PD_{50}$ value could not be calculated.
***$PD_{50}$ estimate of MDV CVI-988 $CEF_{65}$ clone C significantly different from the other two $PD_{50}$ estimates ($p < 0.01$).

EXAMPLE VII

A $PD_{50}$ trial was performed with a CEF adapted virus preparation according to the invention, MDV CVI-988 $CEF_{59}$ clone C. The results are presented in Table 5. On the basis of the conditions mentioned in example VI the results of this assay were statistically comparable with two $PD_{50}$ assays performed with MDV CVI-988 $CEF_{35}$, already presented in Tables 2 and 3 (which results are here presented again).

TABLE 5

Statistical comparison of $PD_{50}$ assays performed with MDV CVI-988 $CEF_{59}$ clone C and two assays with MDV CVI-988 $CEF_{35}$ vaccination.

|  | Vaccine | | |
|---|---|---|---|
|  | MDV CVI-988 $CEF_{59}$ clone C | MDV CVI-988 $CEF_{35}$ | CVI-988 $CEF_{35}$ |
|  | Challenge virus | | |
|  | K | GA-5 | K |
| Highest dose (FFU) | 500 | 500 | 500 |
| Serial dilution in steps | 1:5 | 1:5 | 1:5 |
| Number protected/total |  |  |  |
| Highest dose | 35/36 | 24/27 | 30/30 |
|  | 39/39 | 21/24 | 25/29 |
|  | 27/36 | 18/26 | 22/29 |
|  | 24/40 | 9/23 | 14/30 |
| Lowest dose | 5/38 | 5/22 | 7/30 |
| $PD_{50}$* | 3.6 | 14** | 10.3 |
| 95% Confidence interval of $PD_{50}$ | 0.7–19 | 4.4–44.9 | 3.3–32.1 |
| Slope of probit regressioin line | 1.06 | 0.87 | 1.20 |
| Standard error of slope | 0.23 | 0.23 | 0.29 |

*The number of FFU required to protect 50% of the MD susceptible chickens.
**Significantly higher than $PD_{50}$ of $CEF_{59}$ clone C ($p < 0.05$).

A similar statistical comparison was as well made with the MDV CVI-988 $CEF_{59}$ clone C $PD_{50}$ assay and six assays performed with MDV CVI-988 $CEF_{35}$. The latter $PD_{50}$ trials were described in J. Biol. Standardization 9: 15–22 (1981).

TABLE 6

Comparison of six $PD_{50}$ assays of MDV CVI-988 at about the 35th cell culture passage and MDV CVI-988 CEF 59 clone C.

|  | Trial No. | | | | | | |
|---|---|---|---|---|---|---|---|
|  | $CEF_{59}$ clone C | I | II | III | IV | V | VI |
|  | Challenge virus | | | | | | |
|  | K | K | K | K | K | K | GA-5 |
| Highest dose (FFU) | 500 | 250 | 690 | 690 | 5120 | 276 | 433 |
| Serial dilution in steps | 1:5 | 1:5 | 1:10 | 1:4 | 1:4 | 1:4 | 1:4 |
| Number protected/total |  |  |  |  |  |  |  |
| Highest dose | 35/36 | 29/29 | 36/39 | 10/10 | 22/22 | 15/21 | 19/21 |
|  | 39/39 | 19/26 | 28/39 | 9/10 | 21/21 | 14/19 | 14/21 |
|  | 27/36 | 15/31 | 13/43 | 6/10 | 22/22 | 7/19 | 3/20 |
| Lowest dose | 24/40 | 9/21 | 9/32 | 2/10 | 20/22 | 5/20 | 1/22 |
|  |  |  |  |  | 12/20 | 2/21 | 1/22 |
|  |  |  |  |  | 9/22 | 4/22 |  |
| No vaccine | 5/38 | 7/26 | 17/44 | 3/20 | 4/22 | 5/41 | 0/30 |
| $PD_{50}$* | 3.6 | 35+ | 70+ | 44+ | 16** | 54** | 75+ |
| 95% Confidence | 0.7–19 | 3.4–359 | 16–299 | 17–118 | 1.8–133 | 6.0–483 | 36–159 |

TABLE 6-continued

Comparison of six $PD_{50}$ assays of MDV CVI-988 at about the 35th cell culture passage and MDV CVI-988 CEF 59 clone C.

| | $CEF_{59}$ clone C | I | II | III | IV | V | VI |
|---|---|---|---|---|---|---|---|
| | | | | Challenge virus | | | |
| | K | K | K | K | K | K | GA-5 |
| interval of $PD_{50}$ | | | | | | | |
| Slope of probit regression line | 1.06 | 2.44 | 1.38 | 2.22 | 1.72 | 0.98 | 1.41 |
| Standard error of slope | 0.23 | 1.64 | 0.30 | 0.80 | 0.47 | 0.27 | 0.23 |

*The number of FFU required to protect 50% of the MD susceptible chickens.
**$PD_{50}$ estimate significantly higher than $PD_{50}$ of $CEF_{59}$ clone C (trial IV p < 0.05; trial V p < 0.01).
' Statistical evaluation of differences between $PD_{50}$ estimates not feasible because of different slopes of probit regression lines (trials I and III) or differences in percentage natural protection (trials II and VI).

The following conclusions can be drawn from examples VI and VII:

A statistical comparison was performed with nine pairs of $PD_{50}$ assays in which vaccination was either performed with MDV CVI-988 $CEF_{35}$ or with MDV CVI-988 clone C.

The $PD_{50}$ estimates of $CEF_{59}$ clone C or $CEF_{65}$ clone C preparations were all below those obtained with MDV CVI-988 $CEF_{35}$.

The differences between $PD_{50}$ values were significant in four comparisons (2×p<0.01, 2×p<0.05). In one instance the difference was not significant. In four instances a statistical evaluation was not feasible because of the differences between the compared slopes of probit regression lines or the natural resistance observed in non-vaccinated groups.

It may be concluded that the protective efficacy of MDV CVI-988 clone C is superior to that of MDV CVI-988 $CEF_{35}$ when applied in SPF chickens.

EXAMPLE VIII

A representative of the group of very virulent MD viruses was isolated from a HVT FC126-vaccinated poultry flock in Tunisia. In the flock of origin an MD incidence of 29% had been observed. The isolate (MDV Tun) demonstrated extremely virulent properties, only 100 white blood cells of an infected SPF chicken caused during the standard observation period of 10 weeks over 70% MD losses, as observed by macroscopic observation, in groups of unvaccinated chickens of 9 days of age. The above representative of very virulent MD viruses was employed as challenge virus in two $PD_{50}$ trials in which the protective efficacies of MDV CVI-988 $CEF_{65}$ clone C and HVT FC126 were compared. The results of these trials are presented in Table 7.

TABLE 7

Comparison of protection afforded by MDV CVI-988 $CEF_{65}$ clone C and HVT FC126 against Tun challenge.

| | Vaccine | |
|---|---|---|
| | MDVCVI-988 $CEF_{65}$ clone C | HVT FC126 |
| | Challenge virus | |
| | MDV Tun | MDV Tun |
| Highest dose (FFU) | 268 | 500 |
| Serial dilutions in steps | 1:5 | 1:5 |
| Number of protected/total | | |
| Highest dose | 38/38 | 37/41 |
| | 38/38 | 30/41 |
| | 28/40 | 18/39 |
| Lowest dose | 19/40 | 9/41 |
| No vaccine | 8/38 | 11/39 |
| $PD_{50}$* | 5.2** | 60.8 |
| 95% Confidence interval $PD_{50}$ | 1.6–16.4 | 27.3–136 |
| Slope of probit regression line | 1.75 | 1.35 |
| Standard error of slope | 0.43 | 0.27 |

*The number of FFU required to protect 50% of MD susceptible chickens.
**$PD_{50}$ estimate of MDV CVI-988 $CEF_{65}$ clone C significantly different from HVT FC126 $PD_{50}$ value (p < 0.01).

The conclusion is warranted that the vaccine preparation according to the invention provides better protection to MDV Tun challenge infection as compared to HVT vaccines.

I claim:

1. A virus preparation comprising a live viral clone of Marek's Disease virus, said clone being of the virus MDV CVI-988 $CEF_{65}$ clone C.

2. A virus preparation comprising a live viral clone of Marek's Disease Virus, said clone being selected from the group consisting of MDV CVI-988 $CEF_{65}$ clone C.

3. The preparation of claim 2, which does not comprise any Marek's disease virus belonging to Avian herpesvirus serotype-2 or serotype-3.

4. A method of immunizing chickens against Marek's disease caused by virus strains belonging to avian herpesvirus serotype-1, which comprises inoculating the chickens with a virus preparation of claim 2.

5. The method of claim 4 in which the virus preparation is administered intramuscularly or subcutaneously.

* * * * *

UNITED STATES PATENT AND TRADEMARK OFFICE
CERTIFICATE OF CORRECTION

PATENT NO. : 4,673,572

DATED : Jun. 16, 1987

INVENTOR(S) : Gerben F. De Boer

It is certified that error appears in the above—identified patent and that said Letters Patent is hereby corrected as shown below:

Column 16, claim 2, insert at the end of the claim, --and derivatives of said clone.--

Signed and Sealed this

Fifteenth Day of September, 1987

*Attest:*

DONALD J. QUIGG

*Attesting Officer*   *Commissioner of Patents and Trademarks*